US005463045A

United States Patent [19]

Janssens et al.

[11] Patent Number: 5,463,045

[45] Date of Patent: Oct. 31, 1995

[54] DYES AND DYE-DONOR ELEMENTS FOR THERMAL DYE TRANSFER RECORDING

[75] Inventors: Wilhelmus Janssens, Aarschot; Luc Vanmaele, Lochristi, both of Belgium

[73] Assignee: AGFA-Gevaert, N.V., Mortsel, Belgium

[21] Appl. No.: 248,726

[22] Filed: May 25, 1994

Related U.S. Application Data

[62] Division of Ser. No. 44,041, Apr. 8, 1993, Pat. No. 5,324,621.

[51] Int. Cl.[6] ........................ C07D 215/16; C07D 209/02

[52] U.S. Cl. ........................... 546/158; 546/198; 546/199; 546/201; 548/159; 548/180; 548/215; 548/219; 548/305.1; 548/306.1; 548/309.7; 548/456; 548/505

[58] Field of Search ..................................... 548/468, 159, 548/180, 215, 219, 305.1, 306.1, 309.7, 456, 505; 546/158, 198, 199, 201

[56] References Cited

U.S. PATENT DOCUMENTS

| | | | |
|---|---|---|---|
| 4,954,478 | 9/1990 | Taguchi et al. | 8/471 |
| 5,026,677 | 6/1991 | Vanmaele | 503/227 |
| 5,147,844 | 9/1992 | Weber et al. | 503/227 |
| 5,168,044 | 12/1992 | Shuttleworth et al. | 430/7 |
| 5,324,621 | 6/1994 | Janessen et al. | 430/201 |

*Primary Examiner*—C. Warren Ivy
*Assistant Examiner*—Raymond Covington
*Attorney, Agent, or Firm*—Breiner & Breiner

[57] ABSTRACT

Dye-donor element for thermal dye transfer comprising at least one magenta dye having extremely low side absorption in the blue and red regions of the spectrum, said dye corresponding to the general formula (I):

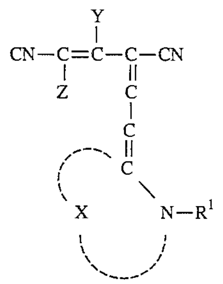

(I)

wherein $R^1$ is H, (cyclo)alkyl, or aryl; X represents the atoms completing a heterocycle; Z is an electron-withdrawing group; Y is an electron-withdrawing group or —$N(R^2)R^3$; $R^2$ and $R^3$ together represent the atoms completing a heterocycle; or $R^2$ and $R^3$ together represent $=C(R^4)R^5$, or each of $R^2$ and $R^3$ represents (same or different) (cyclo)alkyl, aryl, or an electron-withdrawing group; each of $R^4$ and $R^5$ (same or different) represents H, (cyclo)alkyl, aryl, a heterocycle, $SO_2R^6$, $COR^6$, $CSR^6$, $POR^6R^7$, $OR^8$, $NR^8R^9$, $SR^8$, or $R^4$ and $R^5$ together represent the atoms completing an aliphatic ring or a heterocycle, each of $R^6$ and $R^7$ (same or different) represents (cyclo)alkyl, alkenyl, aryl group, alkyloxy, aryloxy, alkylthio, arylthio, amino, a heterocycle, or $R^6$ and $R^7$ together represent the atoms completing a 5- or 6-membered nucleus, and each of $R^8$ and $R^9$ (same or different) represents (cyclo)alkyl, alkenyl, aralkyl, aryl, a heterocycle, or $R^8$ and $R^9$ together represent the atoms completing a 5- or 6-membered nucleus.

2 Claims, No Drawings

DYES AND DYE-DONOR ELEMENTS FOR THERMAL DYE TRANSFER RECORDING

This is a division of application Ser. No. 08/044,041 filed Apr. 8, 1993 now U.S. Pat. No. 5,324,621.

DESCRIPTION

1. Field of the Invention

The present invention relates to dye-donor elements for use according to thermal dye sublimation transfer.

2. Background of the Invention

Thermal dye transfer methods include thermal dye sublimation transfer also called thermal dye diffusion transfer. This is a recording method in which a dye-donor element provided with a dye layer containing sublimating dyes having heat transferability is brought into contact with a receiver sheet and selectively, in accordance with a pattern information signal, heated with a thermal printing head provided with a plurality of juxtaposed heat-generating resistors, whereby dye is transferred from the selectively heated regions of the dye-donor element to the receiver sheet and forms a pattern thereon, the shape and density of which are in accordance with the pattern and intensity of heat applied to the dye-donor element.

A dye-donor element for use according to thermal dye sublimation transfer usually comprises a very thin support e.g. a polyester support, one side of which is covered with a dye layer comprising the printing dyes. Usually, an adhesive or subbing layer is provided between the support and the dye layer. Normally, the opposite side of the support is covered with a slipping layer that provides a lubricated surface against which the thermal printing head can pass without suffering abrasion. An adhesive layer may be provided between the support and the slipping layer.

The dye layer can be a monochromic dye layer or it may comprise sequential repeating areas of differently coloured dyes e.g. dyes having a cyan, magenta, yellow, and optionally black hue. When a dye-donor element containing three or more primary colour dyes is used, a multicolour image can be obtained by sequentially performing the dye transfer process steps for each colour.

A primary coloured dye layer e.g. a magenta or cyan or yellow dye layer may comprise only one primary coloured dye (a magenta, cyan, or yellow dye respectively) or may comprise a mixture of two or more primary coloured dyes of the same hue (two magenta, two cyan, or two yellow dyes respectively).

When multicolour images or multicolour reproductions are made with the so-called substractive colours yellow, magenta, and cyan, the spectral absorption characteristics of the magenta colour dye employed are of great importance. In fact, the side absorptions of the magenta colour dye determine whether it is possible to obtain vivid blue and vivid red and orange colours.

Magenta colour dyes for use in thermal dye diffusion transfer recording have been reviewed in Chemistry and Industry, Oct. 16, 1989, p. 682, FIG. 6 and FIG. 7. Other magenta dyes have been described in JP 60 031,563, EP 441,396, EP 279,467, U.S. Pat. No. 4,698,651, U.S. Pat. No. 4,910,187, the European Patent Applications 92203208.1 and 92203207.3 and in the corresponding U.S. Ser. Nos. 08/138,254 (FWC) to 08/434,409 (pending), and 08/138,250 now U.S. Pat. No. 5,438,030 respectively.

Although the side absorption in the red region of the absorption spectra of these dyes is generally satisfactory, the side absorption in the blue region is rather significant.

As a consequence it is very difficult to produce really vivid blue shades by combination of magenta colour dyes of the prior art with cyan colour dyes.

3. Summary of the Invention

It is therefore an object of the present invention to provide dye-donor elements comprising magenta dyes, which upon thermal transfer of at least part of said magenta dyes to a receiver element yield magenta dyes having extremely low side absorptions in the red and the blue regions of the spectrum.

It is another object of the present invention to provide dye-donor elements, which upon thermal transfer of at least part of said magenta dyes and of cyan and/or yellow dyes to a receiver element yield mixed dye images showing vivid blue, vivid red, and vivid orange colours in the full colour areas.

It is a further object of the present invention to provide a new class of magenta dyes, which have a high extinction maximum and extremely low side absorptions in the red and the blue regions of the spectrum.

Further objects will become apparent from the description hereinafter.

In accordance with the present invention a dye-donor element for use according to thermal dye sublimation transfer is provided, said dye-donor element comprising a support having thereon a dye layer comprising at least one magenta dye, wherein said at least one magenta dye corresponds to the following general formula (I):

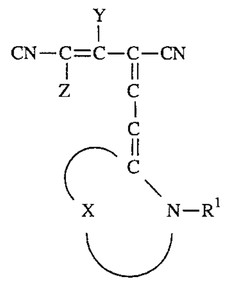

(I)

wherein:

$R^1$ represents hydrogen, a $C_1$–$C_6$ alkyl group, a substituted $C_1$–$C_6$ alkyl group, a cycloalkyl group, a substituted cycloalkyl group, an aryl group, or a substituted aryl group, X represents the atoms needed to complete a heterocyclic nucleus, a substituted heterocyclic nucleus, a heterocyclic nucleus carrying a fused-on cycloaliphatic, aromatic, or heterocyclic ring or ring system, or a substituted heterocyclic nucleus carrying a fused-on cycloaliphatic, aromatic, or heterocyclic ring or ring system, Z represents an electron-withdrawing group, Y represents an electron-withdrawing group or $—N(R^2)R^3$, $R^2$ and $R^3$ have a significance chosen from the following alternatives (1), (2), and (3):

(1) $R^2$ and $R^3$ together represent the atoms needed to complete a heterocyclic nucleus, a substituted heterocyclic nucleus, a heterocyclic nucleus carrying a fused-on cycloaliphatic, aromatic, or heterocyclic ring or ring system, or a substituted heterocyclic nucleus carrying a fused-on cycloaliphatic, aromatic, or heterocyclic ring or ring system, or (2) $R^2$ and $R^3$ together represent the group $=C(R^4)R^5$, or (3) each of $R^2$ and $R^3$, in case they together do not have any of the significances identified under (1) and (2) hereinbefore, represents (same or different) an alkyl group, a substituted alkyl group, a cycloalkyl group, a substituted cycloalkyl group, an aryl group, a substituted aryl group, or an electron-withdrawing group e.g. an acyl group, in case (3) at least one of $R^2$ and $R^3$ being an electron-withdrawing group, each of $R^4$ and $R^5$ (same or different) represents hydrogen, an alkyl group, a substituted alkyl group, a cycloalkyl group, a substituted cycloalkyl group, an aryl group, a substituted aryl group, a heterocyclic nucleus, a substituted heterocyclic nucleus $SO_2R^6$, $COR^6$, $CSR^6$, $POR^6R^7$, $OR^8$, $NR^8R^9$, $SR^8$, or $R^4$ and $R^5$ together represent the atoms necessary to complete an aliphatic ring, a substituted aliphatic ring, a heterocyclic nucleus, a substituted heterocyclic nucleus, a heterocyclic nucleus carrying a fused-on cycloaliphatic, aromatic, or heterocyclic ring or ring system, or a substituted heterocyclic nucleus carrying a fused-on cycloaliphatic, aromatic, or heterocyclic ring or ring system, each of $R^6$ and $R^7$ (same or different) represents an alkyl group, a substituted alkyl group, a cycloalkyl group, a substituted cycloalkyl group, an alkenyl group, a substituted alkenyl group, an aryl group, a substituted aryl group, an alkyloxy group, a substituted alkyloxy group, an aryloxy group, a substituted aryloxy group, an alkylthio group, a substituted alkylthio group, an arylthio, a substituted arylthio group, an amino group, a substituted amino group, a heterocyclic nucleus, or a substituted heterocyclic nucleus, or $R^6$ and $R^7$ together represent the atoms necessary to complete a 5- or 6-membered nucleus, and each of $R^8$ and $R^9$ (same or different) represents an alkyl group, a substituted alkyl group, a cycloalkyl group, a substituted cycloalkyl group, an alkenyl group, a substituted alkenyl group, an aralkyl group, a substituted aralkyl group, an aryl group, a substituted aryl group, a heterocyclic nucleus, or a substituted heterocyclic nucleus, or $R^8$ and $R^9$ together represent the atoms necessary to complete a 5- or 6-membered nucleus.

The present invention also provides novel magenta dyes corresponding to the above general formula I.

The present invention further provides a dyed receiving element comprising a dye in image-wise distribution, formed by thermal dye sublimation transfer using a dye-donor element according to the present invention.

The present invention also provides a method of forming an image by image-wise heating a dye-donor element comprising a support having thereon a dye layer comprising a binder and at least one dye corresponding to the above general formula I, and causing transfer of the image-wise heated dye to a receiver sheet.

4. Detailed Description of the Invention

A non-exhaustive list of dyes corresponding to the above general formula I is given in Table 1 hereinafter.

TABLE 1

| | Dye |
|---|---|
| 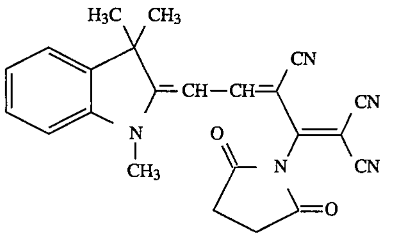 | 1.01 |
| 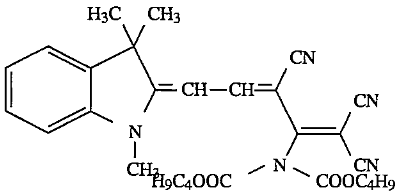 | 1.02 |
| 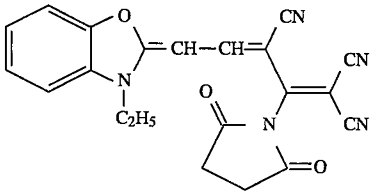 | 1.03 |
| 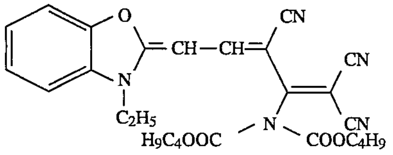 | 1.04 |
| 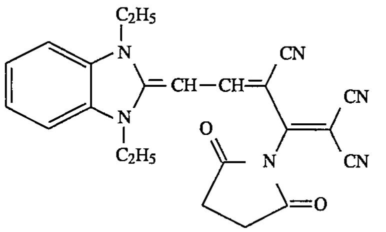 | 1.05 |
| 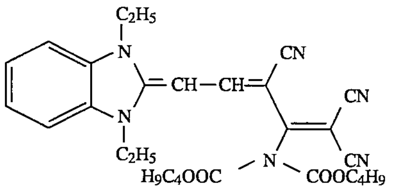 | 1.06 |

TABLE 1-continued

| | Dye |
|---|---|
| 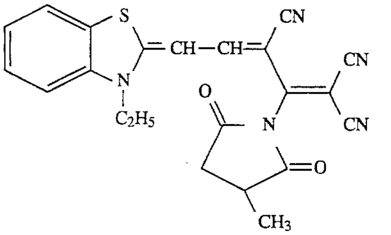 | 1.07 |
| 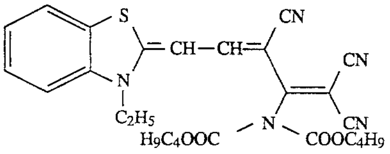 | 1.08 |

TABLE 1-continued

| | Dye |
|---|---|
| 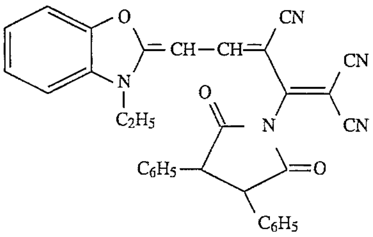 | 1.09 |

According to a preferred embodiment of the present invention the magenta dyes of the present invention correspond to the following general formula II.

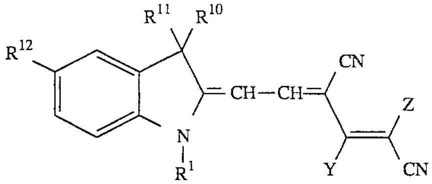

II wherein:

Y, Z, and $R^1$ have the same significances as defined under the above general formula I, each of $R^{10}$ and $R^{11}$ (same or different) represents hydrogen, a $C_1$–$C_6$ alkyl group, or a substituted $C_1$–$C_6$ alkyl group, and $R^{12}$ represents hydrogen or alkyloxycarbonyl.

A non-exhaustive list of dyes corresponding to the above general formula II is given in Table 2 hereinafter.

TABLE 2

| Dye | Z | Y | $R^1 = R^{10} = R^{11}$ | $R^{12}$ |
|---|---|---|---|---|
| 2.01 | $-CN$ | $-N[COOCH_2CH(CH_3)_2]_2$ | $-CH_3$ | $-H$ |
| 2.02 | $-CN$ | $-N[COOCH_2CH_2CH_2CH_3]_2$ | $-CH_3$ | $-H$ |
| 2.03 | $-CN$ | $-N[COOCH_2CH_3]_2$ | $-CH_3$ | $-H$ |
| 2.04 | $-CN$ | 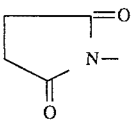 | $-CH_3$ | $-H$ |
| 2.05 | $-CN$ | 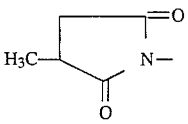 | $-CH_3$ | $-H$ |
| 2.06 | $-CN$ | 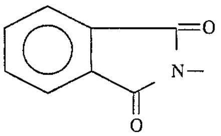 | $-CH_3$ | $-H$ |
| 2.07 | $-CN$ | 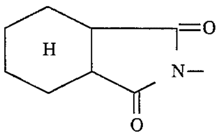 | $-CH_3$ | $-H$ |

TABLE 2-continued
| Dye | Z | Y | $R^1 = R^{10} = R^{11}$ | $R^{12}$ |
|---|---|---|---|---|
| 2.08 | —CN | 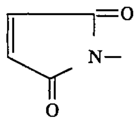 | $-CH_3$ | —H |
| 2.09 | —CN | $(H_3C-SO_2)_2N-$ | $-CH_3$ | —H |
| 2.10 | —CN | 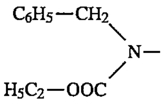 | $-CH_3$ | —H |
| 2.11 | —CN | 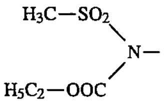 | $-CH_3$ | —H |
| 2.12 | —CN | 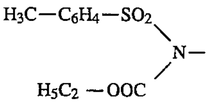 | $-CH_3$ | —H |
| 2.13 | —CN | 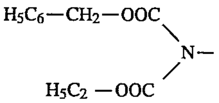 | $-CH_3$ | —H |
| 2.14 | —CN | 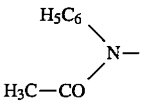 | $-CH_3$ | —H |
| 2.15 | —CN | 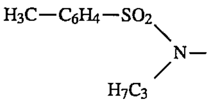 | $-CH_3$ | —H |
| 2.16 | —CN | 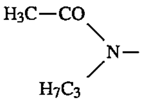 | $-CH_3$ | —H |
| 2.17 | —CN | 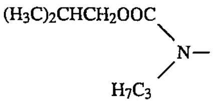 | $-CH_3$ | —H |
| 2.18 | —CN | 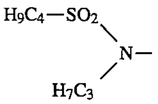 | $-CH_3$ | —H |
| 2.19 | —CN | 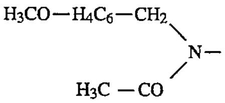 | $-CH_3$ | —H |
| 2.20 | —CN | 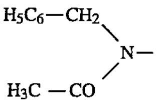 | $-CH_3$ | —H |
| 2.21 | —CN | 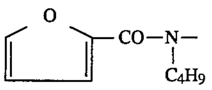 | $-CH_3$ | —H |
| 2.22 | —CN | $(H_3C)_2N-CH=N-$ | $-CH_3$ | —H |

TABLE 2-continued

| Dye | Z | Y | $R^1 = R^{10} = R^{11}$ | $R^{12}$ |
|---|---|---|---|---|
| 2.23 | —CN | 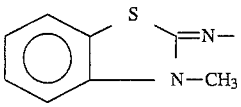 | $-CH_3$ | —H |
| 2.24 | —CN | 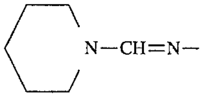 | $-CH_3$ | —H |
| 2.25 | —CN | 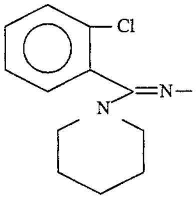 | $-CH_3$ | —H |
| 2.26 | —CN | $-N[COOCH_2CH_2CH_2CH_3]_2$ | $-CH_3$ | $-COOCH_3$ |
| 2.27 | —CN | 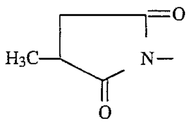 | $-CH_3$ | $-COOCH_3$ |
| 2.28 | —CN | $-N[COOCH_2CH(CH_3)_2]_2$ | $-CH_3$ | $-COOCH_3$ |
| 2.29 | —CN | 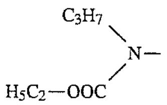 | $-CH_3$ | $-COOCH_3$ |
| 2.30 | —CN | 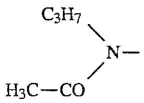 | $-CH_3$ | $-COOCH_3$ |
| 2.31 | —CN | 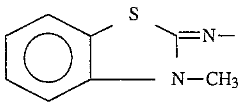 | $-CH_3$ | $-COOCH_3$ |
| 2.32 | —CN | 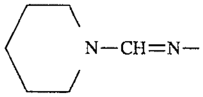 | $-CH_3$ | $-COOCH_3$ |

The dyes corresponding to the general formulae I and II can be prepared by condensation of malononitrile dimer with the corresponding aldehyde followed by derivatization of the amino group according to the synthetic procedures described in U.S. Pat. No. 5,026,677, EP 400,706, and in the European Patent Application 92203979.7 and in the corresponding US Ser. No. 08/035,033 now U.S. Pat. No. 5,324,601.

By way of example the synthesis of dye 2.05 is described in the Preparation example hereinafter.

Preparation Example: Synthesis of Dye 2.05

Dye 2.05 is prepared according to the following reaction scheme.

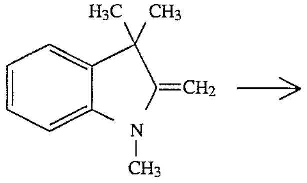

A

-continued

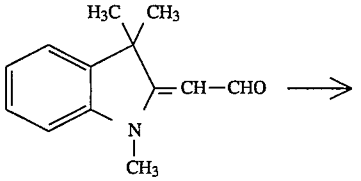

B

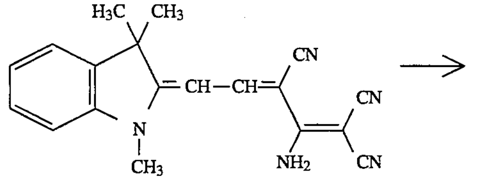

C 37 ml of $POCl_3$ (1.2 equivalent) is added dropwise to a solution of 57 g of 2-methylene-1,3,3-trimethylindoline (A) in 200 ml of dimethylformamide at 0° C. The solution is stirred for 1 h at 20° C. and poured out into a mixture of 250 ml of 10N sodium hydroxide, 750 g of ice, and 700 ml of water. The precipitate is filtered, rinsed with water, and dried.

30 g of the resulting intermediate product B and 21.7 g of manononitrile dimer are dissolved in 100 ml of ethanol. 10.4 ml of triethylamine is added and and the solution is refluxed for 3 h. After cooling the yellow dye C is filtered, rinsed with methanol, and dried.

6.4 g of dye C and 5.8 g of 2-methyl-succinic anhydride are dissolved in 70 ml of dichloromethane and 1 ml of acetic acid.

6.3 ml of triethylamine is added and the solution is stirred for 1 h at 20° C. and for 2 h at 35° C. 75 ml of methanol is added and stirring is continued for 1 h at 20° C.

The precipitate is filtered, rinsed with methanol, and dried.

Yield: 7.5 g of dye 2.05.

The dyes can be used as filter dyes e.g. for silver halide colour photographic materials and also as antihalation dyes. They can further be used in inkjet printing after having been adapted with hydrophilic groups. Furthermore, they can be used for transfer printing on fabrics. They can also be employed for making colour filter array elements as described in U.S. Pat. No. 5,175,069.

According to a preferred embodiment of the present invention these dyes are used as magenta dyes in the dye layer of a dye-donor element for thermal dye sublimation transfer.

The dye layer of the dye-donor element is formed preferably by adding the dyes, a polymeric binder medium, and other optional components to a suitable solvent or solvent mixture, dissolving or dispersing these ingredients to form a coating composition that is applied to a support, which may have been provided first with an adhesive or subbing layer, and dried.

The dye layer thus formed generally has a thickness of about 0.2 to 5.0 μm, preferably 0.4 to 2.0 μm, and the amount ratio of dye to binder generally ranges from 9:1 to 1:3 weight, preferably from 3:1 to 1:2 by weight.

The following polymers can be used as polymeric binder: cellulose derivatives, such as ethyl cellulose, hydroxyethyl cellulose, ethylhydroxy cellulose, ethylhydroxyethyl cellulose, hydroxypropyl cellulose, methyl cellulose, cellulose nitrate, cellulose acetate formate, cellulose acetate hydrogen phthalate, cellulose acetate, cellulose acetate propionate, cellulose acetate butyrate, cellulose acetate pentanoate, cellulose acetate benzoate, cellulose triacetate; vinyl-type resins and derivatives, such as polyvinyl alcohol, polyvinyl acetate, polyvinyl butyral, copolyvinyl butyral-vinyl acetal-vinyl alcohol, polyvinyl pyrrolidone, polyvinyl acetoacetal, polyacrylamide; polymers and copolymers derived from acrylates and acrylate derivatives, such as polyacrylic acid, polymethyl methacrylate and styrene-acrylate copolymers; polyester resins; polycarbonates; copolystyrene-acrylonitrile; polysulfones; polyphenylene oxide; organosilicones, such as polysiloxanes; epoxy resins and natural resins, such as gum arabic. Preferably, the binder for the dye layer of the present invention comprises cellulose acetate butyrate or copolystyrene-acrylonitrile.

The dye-donor element of the present invention can be used for the recording of a coloured image together with primary colour dye-donor elements comprising respectively a magenta dye or a mixture of magenta dyes, a cyan dye or a mixture of cyan dyes and a yellow dye or a mixture of yellow dyes.

Any dye can be used in such a primary colour dye layer provided it is easily transferable to the dye-image-receivng layer of the receiver sheet by the action of heat.

The dyes of the present invention can be used alone or mixed with one another, or even mixed with other primary colour dyes.

Typical and specific examples of other primary colour dyes for use in thermal dye sublimation transfer have been described in e.g. EP 400,706, EP 209,990, EP 216,483, EP 218,397, EP 227,095, EP 227,096, EP 229,374, EP 235,939, EP 247,737, EP 257,577, EP 257,580, EP 258,856, EP 279,330, EP 279,467, EP 285,665, U.S. Pat. No. 4,743,582, U.S. Pat. No. 4,753,922, U.S. Pat. No. 4,753,923, U.S. Pat. No. 4,757,046, U.S. Pat. No. 4,769,360, U.S. Pat. No. 4,771,035, JP 84/78,894, JP 84/78,895, JP 84/78,896, JP 84/227,490, JP 84/227,948, JP 85/27,594, JP 85/30,391, JP 85/229,787, JP 85/229,789, JP 85/229,790, JP 85/229,791, JP 85/229,792, JP 85/229,793, JP 85/229,795, JP 86/268, 493, JP 86/268,494, JP 85/268,495, and JP 86/284,489.

The coating layer may also contain other additives, such as curing agents, preservatives, organic or inorganic fine particles, dispersing agents, antistatic agents, defoaming agents, viscosity-controlling agents, these and other ingredients having been described more fully in EP 133,011, EP 133,012, EP 111,004, and EP 279,467.

Any material can be used as the support for the dye-donor element provided it is dimensionally stable and capable of withstanding the temperatures involved, up to 400° C. over a period of up to 20 msec, and is yet thin enough to transmit heat applied on one side through to the dye on the other side to effect transfer to the receiver sheet within such short periods, typically from 1 to 10 msec. Such materials include polyesters such as polyethylene terephthalate, polyamides, polyacrylates, polycarbonates, cellulose esters, fluorinated polymers, polyethers, polyacetals, polyolefins, polyimides, glassine paper and condenser paper. Preference is given to a support comprising polyethylene terephthalate. In general, the support has a thickness of 2 to 30 μm. The support may also be coated with an adhesive of subbing layer, if desired.

The dye layer of the dye-donor element can be coated on the support or printed thereon by a printing technique such as a gravure process.

A dye-barrier layer comprising a hydrophilic polymer may also be employed between the support and the dye layer of the dye-donor element to enhance the dye transfer densities by preventing wrong-way transfer of dye backwards to the support. The dye barrier layer may contain any hydrophilic material that is useful for the intended purpose. In general, good results have been obtained with gelatin, polyacrylamide, polyisopropyl acrylamide, butyl methacrylate-grafted gelatin, ethyl methacrylate-grafted gelatin, ethyl acrylate-grafted gelatin, cellulose monoacetate, methylcellulose, polyvinyl alcohol, polyethyleneimine, polyacrylic acid, a mixture of polyvinyl alcohol and polyvinyl acetate, a mixture of polyvinyl alcohol and polyacrylic acid, or a mixture of cellulose monoacetate and polyacrylic acid. Suitable dye barrier layers have been described in e.g. EP 227,091 and EP 228,065. Certain hydrophilic polymers e.g. those described in EP 227,091 also have an adequate adhesion to the support and the dye layer, so that the need for a separate adhesive or subbing layer is avoided. These particular hydrophilic polymers used in a single layer in the dye-donor element thus perform a dual function, hence are referred to as dye-barrier/subbing layers.

Preferably the reverse side of the dye-donor element has been coated with a slipping layer to prevent the printing head from sticking to the dye-donor element. Such a slipping layer would comprise a lubricating material such as a surface-active agent, a liquid lubricant, a solid lubricant or mixtures thereof, with or without a polymeric binder. The surface-active agents may be any agents known in the art such as carboxylates, sulfonates, phosphates, aliphatic amine salts, aliphatic quaternary ammonium salts, polyoxyethylene alkyl ethers, polyethylene glycol fatty acid esters, fluoroalkyl $C_2$–$C_{20}$ aliphatic acids. Examples of liquid lubricants include silicone oils, synthetic oils, saturated hydrocarbons, and glycols. Examples of solid lubricants include various higher alcohols such as stearyl alcohol, fatty acids and fatty acid exters. Suitable slipping layers have been described in e.g. EP 138,483, EP 227,090, U.S. Pat. No. 4,567,113, U.S. Pat. No. 4,572,860, U.S. Pat. No. 4,717,711. Preferably the slipping layer comprises a styrene-acrylonitrile copolymer or a styrene-acrylonitrile-butadiene copolymer or a mixture thereof or a polycarbonate as described in European patent application no. 91202071.6 and in the corresponding U.S. Ser. No. . . . , as binder and a polysiloxane-polyether copolymer or polytetrafluoroethylene or a mixture thereof as lubicrant in an amount of 0.1 to 10% by weight of the binder or binder mixture.

The support for the receiver sheet that is used with the dye-donor element may be a transparent film of e.g. polyethylene terephthalate, a polyether sulfone, a polyimide, a cellulose ester or a polyvinyl alcohol-co-acetal. The support may also be a reflective one such as a baryta-coated paper, polyethylene-coated paper or white polyester i.e. white-pigmented polyester. Blue-coloured polyethylene terephthalate film can also be used as support.

To avoid poor adsorption of the transferred dye to the support of the receiver sheet this support must be coated with a special layer called dye-image-receiving layer, into which the dye can diffuse more readily. The dye-image-receiving layer may comprise e.g. a polycarbonate, a polyurethane, a polyester, a polyamide, polyvinyl chloride, polystyrene-co-arcylonitrile, polycaprolactone, or mixtures thereof. The dye-image receiving layer may also comprise a heat-cured product of poly(vinyl chloride/co-vinyl acetate/co-vinyl alcohol) and polyisocyanate. Suitable dye-image-receiving layers have been described in e.g. EP 133,011, EP 133,012, EP 144,247, EP 227,094, and EP 228,066.

In order to improve the light-fastness and other stabilities of recorded images UV-absorbers, singlet oxygen quenchers such as HALS-compounds (Hindered Amine Light Stabilizers) and/or antioxidants can be incorporated into the dye-image-receiving layer.

The dye layer of the dye-donor element or the dye-image-receiving layer of the receiver sheet may also contain a releasing agent that aids in separating the dye-donor element from the receiver sheet after transfer. The releasing agents can also be incorporated in a separate layer on at least part of the dye layer and/or of the dye-image-receiving layer. Suitable releasing agents are solid waxes, fluorine- or phosphate-containing surface-active agents and silicone oils. Suitable releasing agents have been described in e.g. EP 133,012, JP 85/19,138, and EP 227,092.

The dye-donor elements according to the invention are used to form a dye transfer image, which process comprises placing the dye layer of the dye-donor element in face-to-face relation with the dye-image-receiving layer of the receiver sheet and image-wise heating from the back of the dye-donor element. The transfer of the dye is accomplished by heating for about several milliseconds at a temperature of 400° C.

When the process is performed for but one single colour, a monochromic dye transfer image is obtained. A multicolour image can be obtained by using a dye-donor element containing three or more primary colour dyes and sequentially performing the process steps described above for each colour. The above sandwich of dye-donor element and receiver sheet is formed on three occasions during the time when heat is applied by the thermal printing head. After the first dye has been transferred, the elements are peeled apart. A second dye-donor element (or another area of the dye-donor element with a different dye area) is then brought in register with the dye-receiving element and the process is repeated. The third colour and optionally further colours are obtained in the same manner.

In addition to thermal heads, laser light, infrared flash, or heated pens can be used as the heat source for supplying heat energy. Thermal printing heads that can be used to transfer dye from the dye-donor elements of the present invention to a receiver sheet are commercially available. In case laser light is used, the dye layer or another layer of the dye element has to contain a compound that absorbs the light emitted by the laser and converts it into heat e.g. carbon black.

Alternatively, the support of the dye-donor element may be an electrically resistive ribbon consisting of e.g. a multilayer structure of a carbon-loaded polycarbonate coated with a thin aluminium film. Current is injected into the resistive ribbon by electrically addressing a printing head electrode resulting in highly localized heating of the ribbon beneath the relevant electrode. The fact that in this case the heat is generated directly in the resistive ribbon and that it is thus the ribbon that gets hot leads to an inherent advantage in printing speed using the resistive ribbon/electrode head technology as compared to the thermal head technology, according to which the various elements of the thermal head get hot and must cool down before the head can move to the next printing position.

The following examples illustrate the invention in more detail without, however, limiting the scope thereof.

EXAMPLE 1

The absorption maxima ($\lambda_{max}$) and extinction maxima ($\epsilon_{max}$) of the dyes identified below were determined in methanol (unless otherwise indicated). The results are listed in table 3.

TABLE 3

| Dye | $\lambda_{max}$ (nm) | $\epsilon_{max}$ |
|---|---|---|
| 2.01 | 530 | 80400 |
| 2.02 | 529 | 81210 |
| 2.03 | 530 | 77835 |
| 2.04 | 555 | 73648 |
| 2.05 | 555 | 76614 |
| 2.06 | 526 | 72056 |
| 2.07 | 555 | 82578 |
| 2.08 | 532 | 71334 |
| 2.09 | 542[a] | 73546 |
| | 550[b] | 76960 |

[a]: determined in methanol/dichloromethane (1:1)
[b]: determined in dichloromethane

EXAMPLE 2

Receiver sheets were prepared by coating a polyethylene-coated paper support weighing 180 g with a dye-image-receiving layer from a solution in ethyl methyl ketone of 3,6 $g/m^2$ of poly(vinyl chloride/co-vinyl acetate/co-vinyl alcohol) (Vinylite VAGD supplied by Union Carbide), 0,336 $g/m^2$ of diisocyanate (Desmodur N3300 supplied by Bayer AG), and 0,2 $g/m^2$ of hydroxy-modified polydimethylsiloxane (Tegomer H SI 2111 supplied by Goldschmidt).

Dye-donor elements for use according to thermal dye sublimation transfer were prepared as follows:

A solution comprising 0.5% by weight of dye and 0.5% by weight of copoly(styrene-acrylonitrile) (Luran 388S, supplied by BASF, Germany) as binder in ethyl methyl ketone was prepared.

From this solution a dye layer having a wet thickness of 100 um was coated on a polyethylene terephthalate film support having a thickness of 6 μm and carrying a conventional subbing layer. The resulting dye layer was dried by evaporation of the solvent.

The opposite side of the film support was coated with a subbing layer of a copolyester comprising ethylene glycol, adipic acid, neopentyl glycol, terephthalic acid, isophthalic acid, and glycerol.

The resulting subbing layer was covered with a solution in methyl ethyl ketone of 0.5 $g/m^2$ of a polycarbonate having the following structural formula to form a heat-resistant layer:

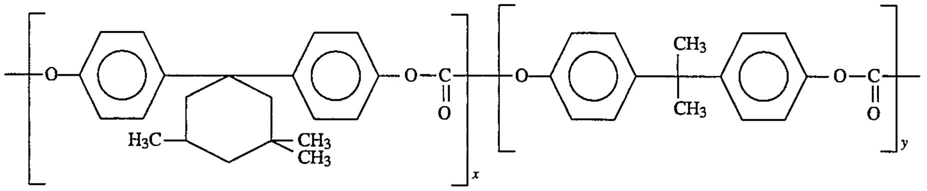

wherein x=55 mol % and y=45 mol %.

Finally, a top layer of polyether-modified polydimethylsiloxane (Tegoglide 410, Goldschmidt) was coated from a solution in isopropanol on the resulting heat-resistant polycarbonate layer.

The dye-donor element was printed in combination with a receiver sheet in a Mitsubishi colour video printer CP100E.

The receiver sheet was separated from the dye-donor element and the colour density value of the recorded image was measured by means of a Macbeth TR 924 densitometer in the red, green, and blue region in Status A mode.

The above described experiment was repeated:

for dyes 2.01 to 2.09 according to the present invention, for the commercially available magenta comparison dyes C.01 to C.04 commonly used in thermal transfer recording (identified in Table 4), and for the dyes C.05 and C.06 identified in Table 4, which are known from the European Patent Applications 92203208.1 and 92203207.3 and the corresponding U.S. Ser. Nos. 08/138,254 (FWC) to 08/434,409 (pending) and 08/138,256 now U.S. Pat. No. 5,438,030 respectively.

TABLE 4

| Comparison dyes | Dye N° |
|---|---|
| 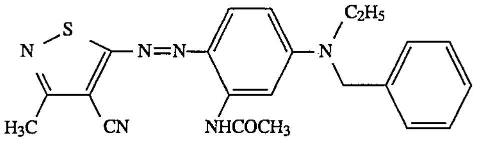 | C.01 |
| 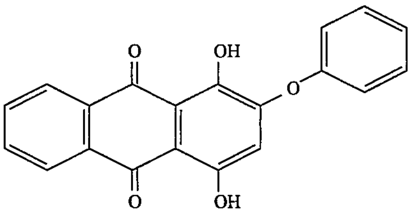 | C.02 |
| 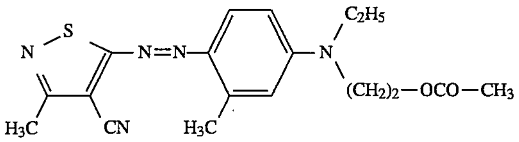 | C.03 |
| 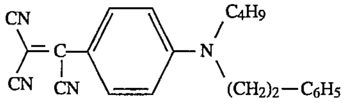 | C.04 |

TABLE 4-continued

| Comparison dyes | Dye N° |
|---|---|
| 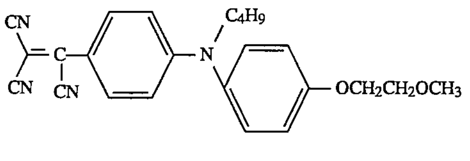 | C.05 |

TABLE 4-continued

| Comparison dyes | Dye N° |
|---|---|
| 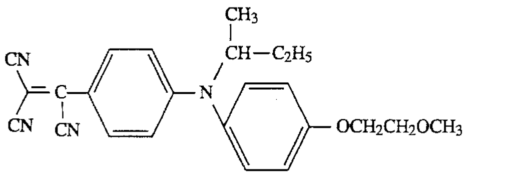 | C.06 |

In Table 5 the spectral characteristics of the dyes are given.

TABLE 5

| Dye | Spectral absorption Filter | | | |
|---|---|---|---|---|
| N° | Red | green | blue | Dmax |
| C.01 | 17 | 150 | 47 | |
| C.02 | 8 | 150 | 57 | |
| C.03 | 13 | iso | 45 | |
| C.04 | 9 | 150 | 34 | |
| C.05 | 20 | 150 | 28 | |
| C.06 | 8 | 150 | 32 | |
| 2.01 | 7 | 150 | 17 | 180 |
| 2.02 | 5 | 150 | 16 | 255 |
| 2.03 | 4 | 150 | 26 | 230 |
| 2.04 | 8 | 150 | 16 | 174 |
| 2.05 | 7 | 150 | 13 | 177 |
| 2.06 | | insoluble | | |
| 2.07 | 6 | 150 | 13 | 169 |
| 2.08 | 6 | 150 | 15 | 207 |
| 2.09 | | insoluble | | |

The results listed in Table 5 show that the magenta dyes according to the present invention have substantially lower side absorptions in the red and the blue regions of the spectrum than the prior art dyes. It follows that the magenta dyes according to the present invention are very suited for high quality colour recording such as the production of colour proofs. They make it possible to form mixed dyes showing vivid blue, vivid red, and vivid orange colours in the full colour areas without the need of a separate special blue printing ink for forming vivid blue shades.

We claim:

1. Dye corresponding to the following general formula (I):

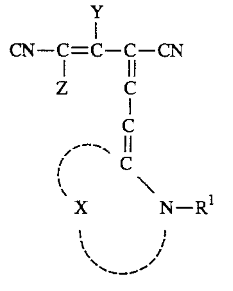

(I)

wherein:

$R^1$ represents hydrogen, a $C_1$–$C_6$ alkyl group, a substituted $C_1$–$C_6$ alkyl group, a cycloalkyl group, a substituted cycloalkyl group, an aryl group, or a substituted aryl group, X represents the atoms needed to complete a polycyclic heterocyclic ring system consisting of a phenyl ring fused to a 5-membered N-heterocyclic ring optionally having one additional heteroatom selected from the group consisting of N, O and S, Z represents an electron-withdrawing group, Y represents an electron-withdrawing group or —$N(R^2)R^3$, $R^2$ and $R^3$ have a significance chosen from the following alternatives (1), (2) and (3):

(1) $R^2$ and $R^3$ together represent the atoms needed to complete a heterocyclic nucleus, a substituted heterocyclic nucleus, a heterocyclic nucleus carrying a fused-on cycloaliphatic, aromatic, or heterocyclic ring or ring system, or a substituted heterocyclic nucleus carrying a fused-on cycloaliphatic, aromatic, or heterocyclic ring or ring system, or (2) $R^2$ and $R^3$ together represent the group $=C(R^4)R^5$, or (3) each of $R^2$ and $R^3$, in case they together do not have any of the significances identified under (1) and (2) hereinbefore, represents (same or different) an alkyl group, a substituted alkyl group, a cycloalkyl group, a substituted cycloalkyl group, an aryl group, a substituted aryl group, or an electron-withdrawing group, in case (3) at least one of $R^2$ and $R^3$ being an electron-withdrawing group, each of $R^4$ and $R^5$ (same or different) represents hydrogen, an alkyl group, a substituted alkyl group, a cycloalkyl group, a substituted cycloalkyl group, an aryl group, a substituted aryl group, a heterocyclic nucleus, a substituted heterocyclic nucleus, $SO_2R^6$, $COR^6$, $CSR^6$, $POR^6R^7$, $OR^8$, $NR^8R^9$, $SR^8$, or $R^4$ and $R^5$ together represent the atoms necessary to complete an aliphatic ring, a substituted aliphatic ring, a heterocyclic nucleus, a substituted heterocyclic nucleus, a heterocyclic nucleus carrying a fused-on cycloaliphatic, aromatic, or heterocyclic ring or ring system, or a substituted heterocyclic nucleus carrying a fused-on cycloaliphatic, aromatic, or heterocyclic ring or ring system, each of $R^6$ and $R^7$ (same or different) represents an alkyl group, a substituted alkyl group, a cycloalkyl group, a substituted cycloalkyl group, an alkenyl group, a substituted alkenyl group, an aryl group, a substituted aryl group, an alkyloxy group, a substituted alkyloxy group, an aryloxy group, a substituted aryloxy group, an alkylthio group, a substituted alkylthio group, an arylthio, a substituted arylthio group, an amino group, a substituted amino group, a heterocyclic nucleus, or a substituted heterocyclic nucleus, or $R^6$ and $R^7$ together represent the atoms necessary to complete a 5- or 6-membered nucleus, and each of $R^8$ and $R^9$ (same or different) represents an alkyl group, a substituted alkyl group, a cycloalkyl group, a substituted cycloalkyl group, an alkenyl group, a substituted alkenyl group, an aralkyl group, a substituted aralkyl group, an aryl group, a substituted aryl group, a heterocyclic nucleus, or a substituted heterocyclic nucleus, or $R^8$ and $R^9$ together represent the atoms necessary to complete a 5- or 6-membered nucleus.

2. The dye according to claim 1 corresponding to the following general formula (II):

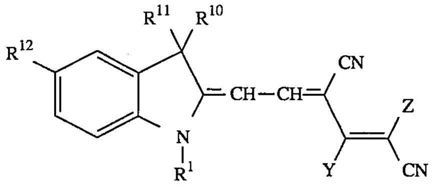
(II)
wherein:
Y, Z, and $R^1$ have the same significances as defined in claim 1,
each of $R^{10}$ and $R^{11}$ (same or different) represents hydrogen, a $C_1$–$C_6$ alkyl group, or a substituted $C_1$–$C_6$ alkyl group, and
$R^{12}$ represents hydrogen or alkyloxycarbonyl.
* * * * *